US011523858B2

(12) United States Patent
Vilims (10) Patent No.: US 11,523,858 B2
(45) Date of Patent: Dec. 13, 2022

(54) SYSTEM AND METHOD FOR RF ABLATION WITH GENERATED IMAGES OF ABLATED TISSUE LESIONS

(71) Applicant: Bradley D. Vilims, Evergreen, CO (US)

(72) Inventor: Bradley D. Vilims, Evergreen, CO (US)

( * ) Notice: Subject to any disclaimer, the term of this patent is extended or adjusted under 35 U.S.C. 154(b) by 312 days.

(21) Appl. No.: 15/675,401

(22) Filed: Aug. 11, 2017

(65) Prior Publication Data
US 2019/0046257 A1  Feb. 14, 2019

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 34/10* (2016.02);
(Continued)

(58) Field of Classification Search
CPC ......... A61B 18/14; A61B 34/10; A61B 90/37; A61B 2034/105; A61B 18/1206; A61B 2018/00434; A61B 2018/0044; A61B 2018/00714; A61B 2018/00791; A61B 2018/00821; A61B 2018/0072; A61B 2018/00761; A61B 2018/00767; A61B 2018/00875; A61B 2034/107
See application file for complete search history.

(56) References Cited

U.S. PATENT DOCUMENTS 5,421,338 A  6/1995  Crowley et al.
6,004,269 A  12/1999  Crowley et al.
(Continued)

OTHER PUBLICATIONS

Cosman, et al., "Bipolar Radiofrequency Lesion Geometry: Implications for Palisade Treatment of Sacroiliac Joint Pain", Pain Practice, Apr. 29, 2010, pp. 3-22, vol. 11, Issue 1, The Authors.
(Continued)

*Primary Examiner* — Michael F Peffley
*Assistant Examiner* — Samantha M Good
(74) *Attorney, Agent, or Firm* — Berg Hill Greenleaf Ruscitti LLP (57) ABSTRACT

The invention includes a system for generating virtual images of proposed and designated areas on a patient's anatomy that are to be treated in a RFA procedure. The images include a size, shape, and location of lesion/ablation patterns. The virtual images include dynamic (developing) or static (developed) lesions selected for the RFA procedure. The images are provided on at least one user interface that superimposes or overlays the lesion pattern(s) on an image of a patient's anatomy that undergoes the procedure. The images can be used to accurately and efficiently conduct RFA procedures and to record the procedures with enhanced visual data to confirm treated tissue areas. The invention further includes a diagnostic method of generating images in preparation for a RFA procedure, and a method of conducting the RFA procedure in which measured parameters determine the size and shape of the ablated areas achieved in the procedure.

13 Claims, 5 Drawing Sheets

(51) Int. Cl.
 *A61B 34/10* (2016.01)
 *A61B 34/00* (2016.01)
 *A61B 90/00* (2016.01)
 *A61B 18/00* (2006.01)
 *A61B 17/00* (2006.01)

(52) U.S. Cl.
 CPC .............. *A61B 34/25* (2016.02); *A61B 90/37* (2016.02); *A61B 2017/00199* (2013.01); *A61B 2017/00221* (2013.01); *A61B 2018/0044* (2013.01); *A61B 2018/0072* (2013.01); *A61B 2018/00434* (2013.01); *A61B 2018/00577* (2013.01); *A61B 2018/00714* (2013.01); *A61B 2018/00761* (2013.01); *A61B 2018/00767* (2013.01); *A61B 2018/00791* (2013.01); *A61B 2018/00821* (2013.01); *A61B 2018/00875* (2013.01); *A61B 2034/105* (2016.02); *A61B 2034/107* (2016.02); *A61B 2090/364* (2016.02); *A61B 2090/376* (2016.02); *A61B 2090/378* (2016.02); *A61B 2090/3762* (2016.02)

(56) References Cited

U.S. PATENT DOCUMENTS

| | | | |
|---|---|---|---|
| 6,950,689 B1 | 9/2005 | Willis et al. | |
| 6,958,064 B2 | 10/2005 | Rioux et al. | |
| 7,037,271 B2 | 5/2006 | Crowley | |
| 7,160,290 B2 | 1/2007 | Eberl et al. | |
| 7,184,811 B2 | 2/2007 | Phan et al. | |
| 7,229,438 B2 | 6/2007 | Young | |
| 7,582,083 B2 | 9/2009 | Swanson | |
| 7,608,072 B2 | 10/2009 | Swanson | |
| 7,727,231 B2 | 6/2010 | Swanson | |
| 7,744,596 B2 | 6/2010 | Young et al. | |
| 7,806,893 B2 | 10/2010 | Ostrovsky et al. | |
| 7,861,725 B2 | 1/2011 | Swanson | |
| 7,962,197 B2 | 6/2011 | Rioux et al. | |
| 8,128,618 B2* | 3/2012 | Gliklich | A61B 8/4411 606/27 |
| 8,175,680 B2 | 5/2012 | Panescu | |
| 8,377,056 B2 | 2/2013 | Oyola et al. | |
| 8,398,623 B2 | 3/2013 | Warnking et al. | |
| 8,409,195 B2 | 4/2013 | Young | |
| 8,571,635 B2 | 10/2013 | McGee | |
| 8,608,734 B2 | 12/2013 | Rioux et al. | |
| 8,617,158 B2 | 12/2013 | Garabedian et al. | |
| 8,792,958 B2 | 7/2014 | Kim et al. | |
| 8,814,855 B2 | 8/2014 | DiCarlo et al. | |
| 8,945,116 B2 | 2/2015 | MacAdam et al. | |
| 8,951,250 B2 | 2/2015 | Young et al. | |
| 2010/0317692 A1 | 12/2010 | Shipe et al. | |
| 2010/0317962 A1* | 12/2010 | Jenkins | A61B 5/055 600/411 |
| 2014/0201669 A1* | 7/2014 | Liu | A61B 18/1815 715/771 |
| 2016/0213282 A1* | 7/2016 | Leo | A61B 18/082 |

OTHER PUBLICATIONS

Schmidt, et al., "Sacroiliac Joint Radiofrequency Ablation with a Multilesion Probe: A Case Series of 60 Patients", Technical Communication, www.anethesia-analgesia.org, Aug. 2014, pp. 460-462, vol. 119, No. 2, International Anesthesia Research Society.

Illumia 3D Programming Algorithm, http://hcp.controlyourpain.com/products/scs-systems/, retrieved from online on Aug. 15, 2017, 1 page.

Illumia 3D Programming Algorithm, Youtube video: https://www youtube.com/watch?v=ERkZd9MYOII, retrieved from online on Aug. 15, 2017, published on Sep. 30, 2015, Boston Scientific.

Illumia 3D Programming Algorithm, https://wn.com/illumina_3d%E2%84%A2_programming_algorithm, retrieved from online on Aug. 15, 2017, published on Oct. 1, 2015.

* cited by examiner

SYSTEM AND METHOD FOR RF ABLATION WITH GENERATED IMAGES OF ABLATED TISSUE LESIONS

FIELD OF THE INVENTION

The invention relates to radiofrequency ablation (RFA) and more specifically to a system and method for visualizing an RFA procedure to specifically show targeted areas of tissue for ablation. Images are generated that show lesion patterns created by the RFA procedures. The images enable medical personnel to better position an RFA device and to more accurately record where the RFA procedure took place.

BACKGROUND OF THE INVENTION

RFA or radiofrequency thermocoagulation neurotomy is a known medical procedure in which neural tissue is ablated using heat generated from a medium frequency alternating current generator. The energy is delivered by a radiofrequency probe or catheter placed within or adjacent to targeted tissue. The radiofrequency energy is then applied to the target tissue causing the tissue surrounding the probe to heat. The temperature attained within the tissue surrounding the radiofrequency probe is monitored via a thermocouple within the probe. Precise temperatures within the tissue can be controlled by adjusting the energy applied to maintain a set temperature. Lesion size and volume of tissue ablated is primarily a function of temperature, and time that the temperature is applied but is substantially influenced by numerous other factors including, but not limited to local, impedance, blood flow, conductivity, size of the probes and their proximity to other RF probes.

RFA procedures are commonly performed under image guidance in order to position a radiofrequency (RF) probe that is used to deliver the RF energy. For example, positioning of the RFA probe may be positioned by using X-ray (fluoroscopy), ultrasound, or a CT scan.

A number of medical procedures can be performed using RFA to include procedures for pain management. RFA for pain management, also be referred to as radiofrequency thermocoagulation neurotomy, may be used to treat various severe chronic pain conditions. The goal in these procedures is to sufficiently heat the nerves transmitting the pain signals so that the nerves are effectively ablated/coagulated and thus no longer capable of propagating a nerve impulse.

RFA is considered a minimally invasive procedure that can be conducted in an outpatient clinic therefore eliminating the need for extended hospital stays and other disadvantages associated with more invasive procedures. Further, the patient may only receive localized anesthesia which avoids general anesthesia and the risks associated therewith.

One well-known type of RFA procedure is one for treating facet joint pain or sacroiliac joint pain caused by injury, arthritis or other degenerative causes. A heat lesion is created on selected nerves with the goal of heating the nerves to an extent which prevents them from effectively transmitting pain signals to the brain. With respect to facet joint pain, a medial branch neurotomy may be conducted to ablate the nerves transmitting pain. With respect to sacroiliac joint pain, a lateral branch neurotomy may be conducted to ablate the nerves transmitting pain.

There are a plethora of patent documents which generally disclose RFA probes and related procedures.

A few examples of US patent references disclosing radiofrequency ablation devices and methods include the U.S. Pat. Nos. 6,554,827; 7,744,596; 9,439,724; 8,551,084 and 9,039,698.

Regarding positioning of radiofrequency ablation devices, the U.S. Pat. No. 9,039,698 discloses an RF ablation system including at least one electromagnetic tracking sensor coil with a magnetic core located in a central lumen of the distal end portion of the cable that delivers radiofrequency energy. The sensor coil communicates with a signal processing unit. An electromagnetic field generator positioned in the vicinity of a patient undergoing treatment generates an electromagnetic field that induces a voltage in the sensor coil. The signal processing unit uses the induced voltage to calculate the position and orientation of the distal end of the catheter in the patient's body.

Despite the known use of imaging guidance to determine the desired position of the RFA probe, it may be difficult for a practitioner to determine exactly where the ablation takes place because the lesion to be created cannot be viewed. Although there may be a slight difference in the density of the tissue after ablation, imaging technologies such as x-ray, ultrasound, and CT scans are not capable of effectively distinguishing between the ablated tissue and surrounding tissue. Therefore, there is no visual record of the area of the tissue actually treated.

Another problem associated with RFA is that while pain relief may be achieved for some patients over a significant period of time (such as 1-2 years), subsequent pain may develop as the nerve tissue regenerates. Further, a single RFA procedure may not adequately ablate the effected nerves so an additional procedure may be required to achieve the desired level of pain management. In this case, a practitioner has to conduct another procedure therefore involving another penetration of the probe into the patient's body. Even within the same procedure conducted, although the practitioner may be highly skilled in locating an RF probe, slight differences in the anatomy between patients makes it very difficult to determine exactly where the ablation will take place as oriented with targeted nerves.

Considering the shortcomings of imaging associated with current RFA procedures, there is a need to provide enhanced imaging in which a practitioner may be able to better visualize the exact shape, location and size of a lesion to be created and the lesion created after the procedure is completed.

There is also need to provide better medical historical information on RFA procedures so that if a patient needs to undergo further treatment, a prior RFA procedure is more accurately recorded in terms of the size and location of ablated tissue area.

Enhanced imaging may also benefit the patient in which the patient is able to better understand the scope of an RFA procedure by providing the patient with easy to view and interpret image of a procedure.

SUMMARY OF THE INVENTION

According to a system of the invention, it includes generating virtual images of proposed and designated ablated tissue areas as oriented on a patient's anatomy. The virtual images include the size, shape, and location of ablated tissue areas to be created in an RFA procedure. The virtual images may further include a description of the size, shape, location where ablation has taken place and supplemented with data including, but not limited to, settings used on an RF generator, parameters monitored during the procedure such as impedance and rate of impedance change, and rate and rise of temperature attained, and the type, number, and relative orientation/relationship of the RF probe(s) used in the procedure. The proposed images can be further defined as those images that are representative of the size and shape of a desired ablation pattern to be achieved in the procedure, and are made available to a user by at least one visual user interface which superimposes or overlays the selected ablation pattern(s) on the same image taken of the patient prior to undergoing the procedure. For example, once an initial image is taken of the patient just prior to the procedure, a practitioner may select a desired ablation pattern in which the ablation pattern is centered/aligned at the location where the practitioner desires to execute the ablation. The designated images can be further defined as those images that are representative of the selected ablation pattern(s) that should have been created in which various measured parameters are used to calculate or otherwise determine the size, shape, and location of the actual ablation pattern that was created. In this regard, the designated images are still "virtual" in that the actual ablated tissue is not revealed in the imaging but rather, the designated images are reliable and accurate representations of the actual ablation patterns created.

According to the system and method of the invention, a computer processor is used to estimate or calculate the ablated tissue or lesion areas as a function of, but not limited to, the specifications of the RF probe used, the energy applied to the specific locations within the patient's body, the target tissue temperature attained, and the duration of time the energy is applied. The energy is applied through an RF generator that serves as the power source for the transmitted energy and the RF generator communicates with the computer processor to convey data regarding the amount of RF energy and duration transmitted through the RF probe that is used to deliver the energy to ablate targeted tissue.

According to a method of the invention, it includes generating the virtual images in which programmable instructions associated with a computer processor are able to mathematically estimate reliable data corresponding to the size, shape, and location where ablation is to be conducted and where ablation has been conducted.

The RF generator is used to generate the energy transferred to a RF probe. A practitioner may select the energy to be applied to the patient over a period of time to effectively ablate targeted tissue. According to the invention, a practitioner may preselect the amount of energy either before or after the RF probe has been positioned, and a virtual image can be created which provides an accurate estimate as to the size, shape, and location where the ablation will take place. From this "pre-procedure" virtual image, the practitioner may adjust the location of the probe within the patient and may adjust the amount of energy to be supplied in order to adjust optimal sizes and locations for the lesions to be created.

After the procedure has taken place, additional virtual images may be created which indicate the size, shape, and location where lesions have been created based upon data captured from the RF generator which includes the duration and level of energy supplied to the RF probe. These virtual images may then form part of the permanent medical record of the patient in which the procedure records are accompanied by the virtual images.

According to another aspect of the invention, it includes a mapping function of the particular anatomy of the patient in order to better predict the location of nerves to be treated and therefore, the RF probe may be more precisely positioned for delivering energy for ablation. According to this mapping function, images taken of the patient prior to the procedure may include measurements of the particular bone structure, and these measurements are used to generate virtual markers on the imaging used in the procedure to provide more accurate positioning of an RF probe. This mapping function may further include generating virtual images of the locations of nerves that should be present considering the particular size and shape of the measured bone structure and visualized anatomic landmarks.

The size, shape, and location of the lesions are generally a function of the particular RF probe being used in which the probe has active electrodes which transmit the energy to the surrounding tissue. Accordingly, the system and method of the invention take into consideration the particular pattern(s) of lesions that can be created by the particular RF probe(s) being used in the procedure.

According to the programming instructions associated with the computer processor of the invention, pre-recorded data provides reliable parameters as to the size and shape of ablated tissue which will result when sufficient amounts of energy are generated. For example, with a RF probe of a known dimension with respect to active areas on the probe that can generate lesions, along with a known amount and duration of energy supplied, the surrounding tissue type (bone, fat, blood, air, etc.), tissue impedance, and temperature attained, a very reliable estimated lesion shape and size can be determined. This lesion shape and size can be transformed into a virtual lesion image which is superimposed over the imaged probe inserted within the patient. The virtual lesion image provides a practitioner with a very accurate three-dimensional estimate as to the size, shape, and location of a lesion that can be created. Based upon this virtual lesion image, a practitioner may choose to adjust the positioning of the RF probe or to adjust the amount of energy supplied to therefore adjust the particular size, shape, or location of the lesion to be created.

In one preferred embodiment, the invention may be considered a system comprising a RF probe, a RF generator, a computer processor with programming instructions for determining a lesion shape and size based on preselected parameters associated with RF energy delivered through the probe, and a visual display that shows a proposed or designed lesion and a lesion that was created during an RFA procedure.

According to another preferred embodiment, a sub-combination of the system is provided comprising the computer processor with programming instructions and the visual display.

According to another preferred embodiment, the invention may be considered a method of generating an image of a lesion designed for an RFA procedure to be conducted and an image of a lesion created by the procedure.

According to one particular method of the invention, it may be considered a diagnostic method for determining optimal location(s) for lesions to be created in a subsequent RFA procedure. According to a first aspect of this diagnostic method, it does not require an actual treatment step to make the determination of optimal locations for the lesions to be created. According to another aspect of this diagnostic method, it may include depicting visual images of one or more RF probes as emplaced within a patient and then adjusting the positioning of the probes as necessary to achieve generation of lesions according to the preselected virtual lesion images. Therefore, it should be understood that this particular method of the invention may be considered a diagnostic method in which a first aspect does not involve actual treatment of the patient and another aspect that includes treatment.

According to this diagnostic method, a practitioner first determines an optimal lesion configuration to be created during the RFA procedure. This is provided to the practitioner in the form of a plurality of virtual lesion images that the practitioner may view on a user interface. Accordingly, a menu of virtual lesion images can be provided to practitioner based upon the type of procedure to be conducted, and the particular medical condition that is sought to be treated. These virtual lesion images correspond to pre-set RF generator settings, along with a selected RF probe that can generate the particular lesion configuration selected. After selection of a desired lesion pattern or configuration, the selected lesion pattern may be superimposed over a virtual image of the patient's anatomy where the RFA procedure is to be conducted. This virtual image of the patient's anatomy can be selected from a number of pre-generated images of human anatomy so that the selection of the lesion pattern can be confirmed as being optimal for the patient's anatomy. Alternatively, an actual image of the patient's anatomy can be used, and the selected lesion pattern is superimposed over the image of the patient. This actual patient image can be obtained prior to the actual procedure being conducted, and may be any type of appropriate image which enables a practitioner to best view the precise location of the lesion to be created with respect to the desired effect of the procedure. Further, a virtual image of the RF probe as it should be positioned to achieve the selected lesion may also be added to the virtual image. Accordingly, the practitioner is able to view a particular location and orientation of the RF probe that will enable the selected lesion pattern to be generated. At this stage, a complete virtual image can be provided prior to the procedure in which the selected lesion pattern is viewable along with optimum positioning of the RF probe to achieve the selected lesion pattern.

According to a further aspect of this method, the practitioner may then emplace the RF probe so that the placement of the RF probe matches the virtual image of the RF probe. In this regard, actual placement of the RF probe as compared to the virtual image of the RF probe would result in a substantial overlap of the RF probe virtual image as compared to the actual placement of the RF probe. If there was any significant misalignment, the practitioner could choose to reposition the probe, or to select another lesion pattern if repositioning of the probe would be problematic. In the latter circumstance, the practitioner could return to a menu selection on the user interface to select another lesion pattern that can be achieved by the actual placement of the RF probe and one which could be deemed acceptable for achieving the desired treatment. According to another step in this method, after the RFA procedure has been completed, a record of the procedure can be created in which the virtual image of the lesion pattern is superimposed over image(s) of the treated patient area. Based upon the accuracy of the system, it is contemplated that the actual lesion pattern created will closely match the virtual lesion pattern selected.

With respect to use of actual images of the patient's anatomy, these images can be imported from the imaging source to the computer processor of the system. The computer processor can then generate instructions for creating a user display for viewing in which the imported image has anatomic landmarks and/or known RF probe measurements or markings. These measurements/markings can be used to synchronize the image magnification on the user display with the actual anatomic image and the images of a virtual RF probe and virtual lesion size. In this way, the composite image produced in the user display shows the anatomic image at an accurate size with the selected virtual lesion and virtual RF probe. Additionally, the RF probe(s) actually used in a procedure could have features that allow the RF generator to conduct a confirmatory verification that the anatomy and probe size(s) were the same magnification and relative size.

According to another aspect of the invention, it is also contemplated that lesion patterns and configurations can be combined by use of two or more RF probes used within the procedure. For example, if a particularly large lesion pattern must be created, the best solution may be the use of two RF probes working in tandem to create the large lesion pattern. In this regard, user interfaces are provided to the practitioner may also provide combinations of individual lesion patterns to create larger sized lesions.

Considering the above features of the invention, in one aspect, it may be more specifically considered a system for generating images representative of areas treated by radiofrequency (RF) ablation, comprising: a computer processor including a memory, a processing element, and programmable instructions including at least one mathematical relationship for visually modeling a size and shape of a selected lesion pattern; an RF probe communicating with said computer processor; an RF generator for supplying energy to said RF probe; said mathematical relationship including variables incorporated in said mathematical relationship including (a) specifications for said RF probe to be used in an ablation procedure, (b) an amount of energy supplied through the RF probe during the ablation procedure, and (c) a measured amount of time in which the energy is supplied; and a visual display for viewing virtual images corresponding to at least one selected lesion pattern.

According to another aspect of the invention, it may be further considered a method for generating images representative of areas treated by radiofrequency (RF) ablation, comprising: providing a computer processor including a memory and a processing element; providing programmable instructions including at least one mathematical relationship for visually modeling a size and shape of a selected lesion pattern; providing communications between an RF probe and said computer processor; generating power for delivery to said RF probe by an RF generator; determining in said mathematical relationship a plurality of variables to achieve said modeling, said variables at least including (a) specifications for said RF probe to be used in an ablation procedure, (b) an amount of energy supplied through the RF probe during the ablation procedure, and (c) a measured amount of time in which the energy is supplied; and producing a dynamic (developing lesion), and/or static visual display including virtual images corresponding to at least one selected lesion pattern.

According to yet another aspect of the invention, it may be considered a subsystem for generating images representative of areas treated by radiofrequency (RF) ablation, comprising: a computer processor including a memory, a processing element, and programmable instructions including at least one mathematical relationship for visually modeling a size and shape of a selected lesion pattern; and said mathematical relationship including variables incorporated in said mathematical relationship including (a) specifications for an RF probe to be used in an ablation procedure, (b) an amount of energy supplied through the RF probe during the ablation procedure, and (c) a measured amount of time in which the energy is supplied; and a visual display for viewing virtual images corresponding to at least one selected lesion pattern.

According to yet another aspect of the invention, it may include generating dynamic virtual images of a lesion configuration as it is being created during a procedure. Arithmetic modeling can be provided in which a lesion size and shape can be incrementally shown on the user display to keep the practitioner advised as the ablation takes place. The dynamic virtual images could be progressive, time-based images in which the size of a selected lesion is shown to increase over time as RF energy continues to be provided through the RF probe(s). These dynamic virtual images allow the practitioner to confirm that the selected lesion is likely to be created in which real-time measured parameters are made available to support data for one or more algorithms used to ultimately generate the time-based images. If a selected lesion is not forming as planned, the practitioner has the option of altering the RF generator settings to make up for any unplanned departures in the formation of the selected lesion.

Although the system and method are particularly disclosed with respect to ablation of nerve tissue, the invention is not limited to just nerve ablation. The system and method of the invention is also applicable to selecting lesions to be created for ablative therapy associated with treatment of other tissue such as tumors, uterine lining tissue, endometrial tissue, and others.

DETAILED DESCRIPTION

According to the system of the invention, the system produces virtual images of proposed and designated ablated tissue areas as oriented on a patient's anatomy. The virtual images include the size, shape, and location of ablated tissue areas for an RFA procedure. The virtual images may be supplemented with data such as a description of the size, shape and location of the ablated tissue areas.

Figure 1:
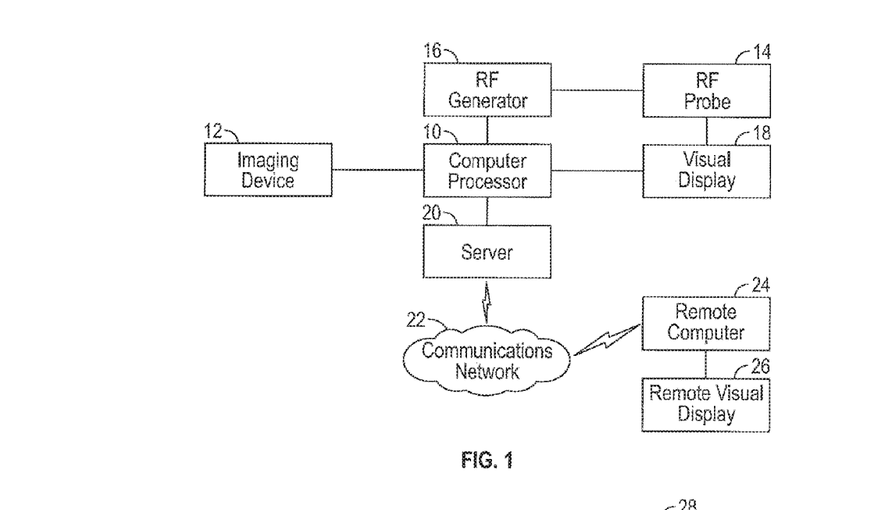
FIG. 1 is a schematic diagram of a system of the invention and a communications network associated with the system.

Referring to a first preferred embodiment as illustrated in FIG. 1, the system includes a computer processor 10 that communicates with an imaging source, such as an X-ray, CT, or ultrasound imaging device 12. The imaging device 12 provides real time images of a patient's anatomy where the RFA procedure takes place. A practitioner inserts and positions a RF probe 14, under imaging guidance, at the location where treatment is to occur. The energy supplied to the RF probe 14 is a RF generator 16 that has a plurality of settings that allows the practitioner to select the amount and duration of the energy supplied to the RF probe 14. The practitioner selects the parameters for energy delivery to the RF probe along with a desired lesion pattern available based on the type of RF probe being used.

RF probes differ as to the active areas on the probes that can generate heat. These active areas are a function of the number and spacing of electrodes on the RF probe as well as a selected bipolar or monopolar configuration when energy is applied.

The determination of the specific size and shape of a lesion can be derived from empirical data in which temperature, energy applied (as measured by amperage, voltage or induction) and the duration of time in which the energy is applied, are measured variables that can be incorporated in one or more algorithms. This data and applied algorithm(s) along with specifications for the particular RF probe/probes and their orientation and proximity to one another) used can be combined to accurately estimate size and shape parameters for the lesion.

According to the invention, it is contemplated that one or more user interfaces are made available to the practitioner so that a plurality of lesion patterns can be selected to include a description of the lesion shapes and/or virtual visual images that represent the general shape of the lesion options. The size of the lesion created is primarily a function of the amount of energy applied through the RF probe and the duration of time applied. A practitioner may also select the size of the lesion to be created in which the practitioner also chooses temperature and duration parameters to determine a desired lesion size.

After the practitioner sets the lesion pattern(s) to be created during a procedure, the computer processor facilitates a virtual image function in which the selected lesion pattern(s) are superimposed or overlaid on the image of the patient. Optionally, the image may include a virtual image of the RF probe to be emplaced during this lesion selection process. The virtual image of the RF probe and virtual image of the selected lesion pattern(s) is viewable on a visual display 18 associated with the processor 10 or a display. At this point, the practitioner can evaluate the size and location of the virtual images to confirm the lesion pattern selected has proper coverage for denervating the selected nerve, nerve tissue, or other tissue to be ablated. Assuming the practitioner is satisfied with the proposed lesion pattern(s), the RFA procedure commences in which the RF probe is emplaced in the patient.

Another set of images can be produced that shows the virtual RF probe and virtual lesion pattern as compared to the actual position of the probe. In this way, the actual position of the RF probe can be compared to the virtual probe position to confirm that the desired lesion pattern will be created. If there is some misalignment, the practitioner may wish to re-insert the probe or to select another lesion pattern that may be acceptable based on the actual position of the RF probe.

After the practitioner determines that the actual position of the probe is acceptable along with an acceptable selected lesion pattern, the RF probe is energized to ablate the targeted tissue.

When the procedure is completed, the processor 10 communicates with the RF generator 16 to confirm the amount of energy supplied and the duration. From these parameters, another virtual image can be produced to confirm the lesion pattern created by superimposing yet another image of a virtual lesion pattern on the patient's anatomy that was imaged during the procedure. This designated lesion pattern may then be made part of the patient's medical record.

In order to further clarify or otherwise enhance the images of the lesion patterns, it is also contemplated that a mapping function can be used to delineate boundaries on the patient's anatomy where nerve bundles are located, and these nerve bundles are provided also as a virtual image in which the lesion patterns can be shown to cover the corresponding nerve bundles. For example, nerve bundles can be shown as small tubular members in various branch configurations, and the virtual image of the lesion pattern(s) are shown with the nerve bundle images. In this way, a practitioner can better visualize the lesion patterns as directly associated with the location of targeted nerves.

The mapping function relates to measurements taken of the bone structure of the patient in which anatomic landmarks/boundaries on the bone structure are recorded and measured. From these measurements, accurate estimates can be made as to the location of various nerve branches and these can then be converted to virtual images for viewing. The mapping function may use fiducial markers coupled with measurement algorithms that can accurately estimate the location(s) of nerve bundles.

Returning to the schematic diagram of FIG. 1, other elements of the system are shown to include a computer server 20 that communicates between the computer processor 10 and a communications network 22. The communications network 22 may represent any electronic communications network such as the Internet, a local area network (LAN), a virtual private network (VPN), and others. The computer processor 10 can upload data to the server 20 which in turn makes the data available through the communications network 22 so that the images recorded during a procedure are made available as part of the patient's medical records. Healthcare providers and other practitioners may require access to the recorded images, as well understood by those associated with the transfer of electronic medical records. FIG. 1 also shows a remote computer 24 with a remote virtual display 26, such as a remote computer associated with another practitioner who may be consulted regarding the results of the RFA procedure. It should therefore be understood that the electronic imaging produced by the computer processor 10 may be electronically transferred to other parties in accordance with known electronic transfer protocols.

It should also be understood however that the system of the invention does not require the server, communications network, remote computer, or remote visual display. Therefore, the computer processor 10 and the visual display 18 may be considered a sub-combination with separate utility. Other sub-combinations of the system may include selected combinations of the functionalities associated with the computer processor 10, imaging device 12, RF generator 16, RF probe 14, and visual display 18.

Figure 2:
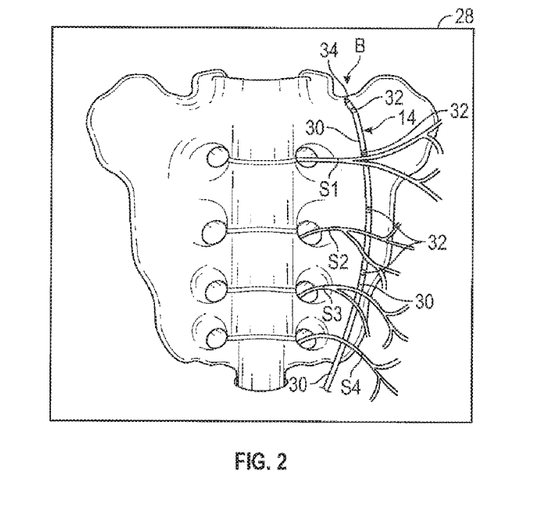
FIG. 2 represents an image of a patient's anatomy and a RF probe positioned for a RFA procedure.

FIG. 2 is a user interface 28 with a representation of an image of a patient's anatomy and a RF probe positioned for a RFA procedure. This user interface is one that may be viewed on the visual display 18 or remote visual display 26. The image shows a bone structure B, such as the sacral bone area and a plurality of nerves S1, S2, and S3 representing the sacral lateral branch nerves associated with the sacroiliac joint. Under known imaging techniques, the nerves are not visible, so these nerves as depicted in the figure are virtual nerves generated by the computer processor 10 in conjunction with mapping or other techniques which may be adopted to virtually locate the assumed position of various nerves with respect to the actual image of the bone structure B. FIG. 2 also shows the body of an RF probe 30, the probe 30 having a plurality of electrodes 32 which define active areas of the probe at the electrodes and the spaces between the electrodes. The distal tip 34 of the probe is located such that a significant portion of the active area of the RF probe is positioned to ablate the lateral branch nerves of S1, S2, and S3. The image of the probe 30 may be a virtual image of a desired position for an actual probe, or the image of the probe may represent the actual probe as it has been emplaced within the patient. In the case of a virtual image of the probe, this is a particular placement and orientation selected by the practitioner which may most optimally ablate the targeted nerve tissue. As mentioned, when the actual probe is emplaced during the procedure, the actual image of the probe may be superimposed or overlaid over the virtual image of the probe so that the practitioner can confirm appropriate positioning of the probe. In addition to the image shown, explanatory text and/or positioning data (not shown) can be included on the visual display.

Figure 3:
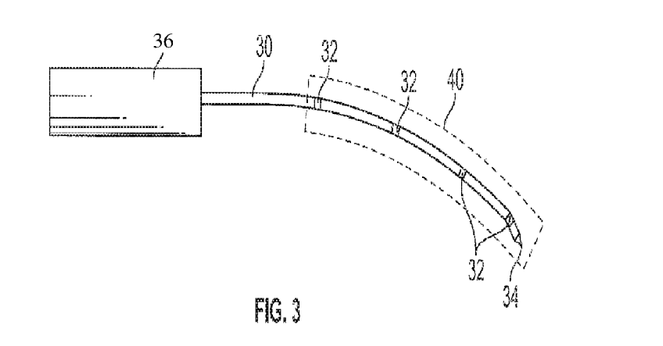
FIG. 3 is an example RF probe illustrating the active portion thereof that can generate a lesion pattern when active.

FIG. 3 is an example of a simplified RF probe illustrating the active portion thereof that can generate a lesion pattern when active. More specifically, FIG. 3 shows the RF probe with a handle 36 and the body of the probe 30 extending from the handle, along with a plurality of electrodes 32 that are selectively based along a length of the probe 30. The lesion pattern is represented by the area bounded by the dashed lines 40. This lesion pattern 40 is shown as extending along a significant length of the probe between the portions between the electrodes 32. This lesion pattern may be provided to a practitioner as its own selectable lesion pattern accompanying the particular RF probe to be used in the procedure. It should be understood that the particular depiction of the lesion pattern 40 is simply exemplary, and the actual lesion that can be created by the probe may not be as uniform and symmetrical. For example, the actual lesion pattern that may be produced by the probe may likely have outer boundaries thereof that are curved and/or a plurality of curved outer boundaries which intersect one another.

Figure 4:
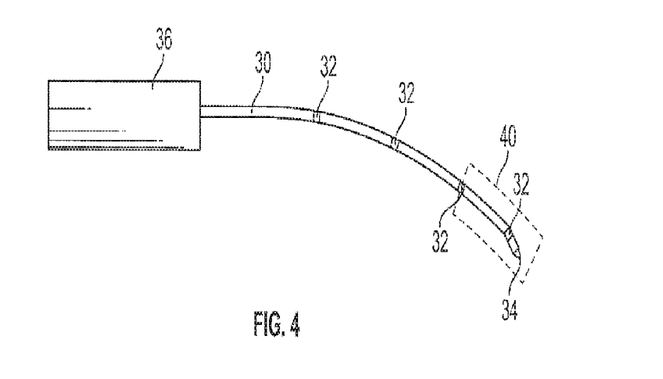
FIG. 4 is the example RF probe illustrating another action portion thereof that can generate a different lesion pattern.

FIG. 4 shows the example RF probe with a different active portion that can generate a different lesion pattern. In this specific example, the lesion pattern 40 is much smaller and only traverses along the distal end of the probe. If the practitioner desired to have a much smaller sized lesion pattern, then the practitioner would also have this option to select.

Figure 5:
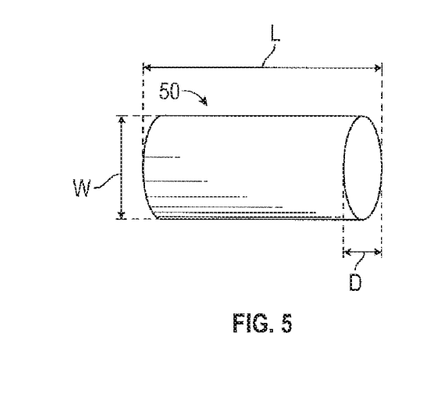
FIG. 5 is a schematic representation of an example virtual lesion pattern that can be superimposed on an image taken of a patient's anatomy in order to confirm the tissue area ablated during an RFA procedure.

FIG. 5 is a schematic representation of an example virtual lesion pattern 50 that can be superimposed on an image taken of a patient's anatomy in order to confirm the tissue area to be ablated during an RFA procedure. As shown, this virtual lesion pattern includes a length L, a width W, and a depth or diameter D. As with the example lesion patterns of FIGS. 3 and 4, the lesion pattern 50 is simplified in its illustration as corresponding to a general geometric shape; however, it should be understood that the actual lesion pattern will have outer boundaries which are curved and/or that may not have exact boundary delineation.

FIG. 5 is also intended to show that with any lesion pattern, there is a three-dimensional effect of an activated RF probe in creating a lesion on the surrounding tissue such that a volumetric pattern is covered. It should be further understood that tissue outside of a lesion pattern is also heated, and there may be some tissue that is heated to an extent that it may become partially ablated. However for purposes of the present invention, the depicted virtual lesion patterns are intended to represent those areas that are sufficiently heated to destroy or otherwise interrupt the functioning of nerves within the depicted virtual lesion patterns.

Figure 6:
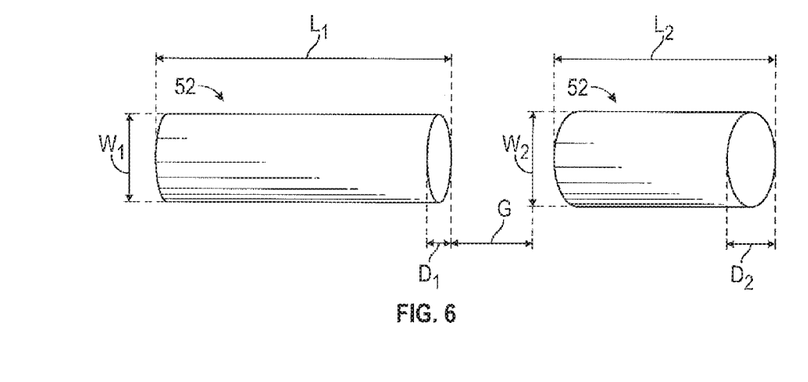
FIG. 6 is a schematic representation of another example virtual lesion pattern that can be superimposed on an image of a patient's anatomy.

FIG. 6 is a schematic representation of another example virtual lesion pattern 52 that can be superimposed on an image of a patient's anatomy in order to confirm the area to be ablated. In this example, the lesion pattern comprises two separate lesions each having their respective lengths (L1, L2), widths (W1, W2), and depths or diameters (D1, D2). The lesions are shown as being separated by a known gap G. This virtual lesion pattern 52 is therefore intended to indicate that a practitioner may select a lesion pattern in which there is discontinuous lesioning.

Figure 7:
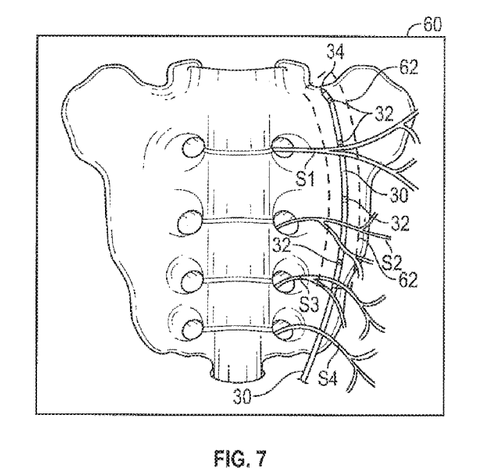
FIG. 7 represents an image of a patient's anatomy with a first example virtual lesion pattern generated by a RF probe.

FIG. 7 is another user interface 60 with a representation of an image of a patient's anatomy with a first example virtual proposed lesion pattern 62. This lesion pattern 62 may also represent a designated virtual lesion pattern. The size and shape of this lesion pattern 62 is similar to the lesion pattern 40 in FIG. 3 in which a significant length of the RF probe body 30 is activated. The targeted nerve bundles are lateral branch nerves from S1, S2, and some of S3.

Figure 8:
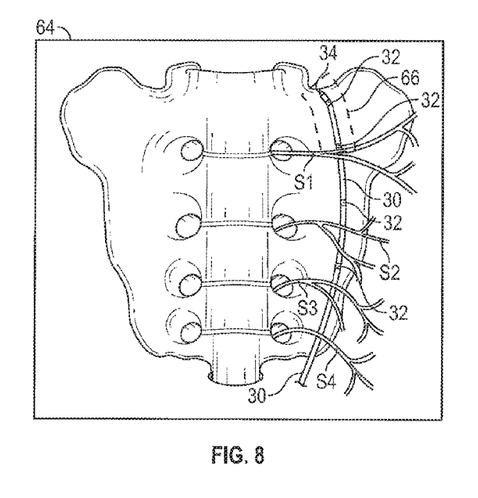
FIG. 8 represents another image of the patient's anatomy with a second example virtual lesion pattern.

FIG. 8 is another user interface 64 with a representation of an image of a patient's anatomy with a second example virtual proposed or virtual designated lesion pattern 66 This lesion pattern is similar to the lesion pattern 40 of FIG. 4 in which the activated portion of the RF probe is at the distal end. In this case, the targeted nerve bundle is the lateral branch nerves of S1.

FIGS. 7 and 8 are intended to show that proposed and/or designated lesion patterns are superimposed or overlaid on the images of the patient's body to provide detailed imaging of an RFA procedure. Instead of having images of the patient's anatomy with just the location of the RF probe, the proposed and designated lesion pattern representations on the images show treated areas. Having the ability to generate virtual images of treated areas in the present invention that cannot be distinguished from non-treated areas with current imaging technology provides great benefits to a practitioner and patient.

With respect to computer programming functions which enable virtual images to be created, empirical data is quantified such that numerical relationships can be determined regarding the size and shape of lesions that can be created considering the particular type of RF probe being used along with the amount of energy delivered over time. One or more algorithms may be developed which can reliably predict how actual ablation will occur. For example, the algorithms could include various differential equations which take into consideration variables such as the energy delivering capacity of a particular type of RF probe along with the amount of energy delivered over time. From these equations, virtual images can be selectively generated to provide a user with a particular lesion pattern that can be produced according to selected parameters which are corresponding variables in the equations.

From this virtual imaging determining process, the selected lesion pattern(s) making up proposed lesion patterns can be superimposed over images of the patient. As mentioned, once the RFA procedure has been conducted, the designated virtual images are created which are reflective of the actual conditions under which the RFA procedure took place. The one or more variables such as the amount of energy supplied and the duration are then used within the algorithms to create the designated lesion patterns that can be assumed to accurately reflect the actual tissue areas ablated during the procedure.

Figure 9:
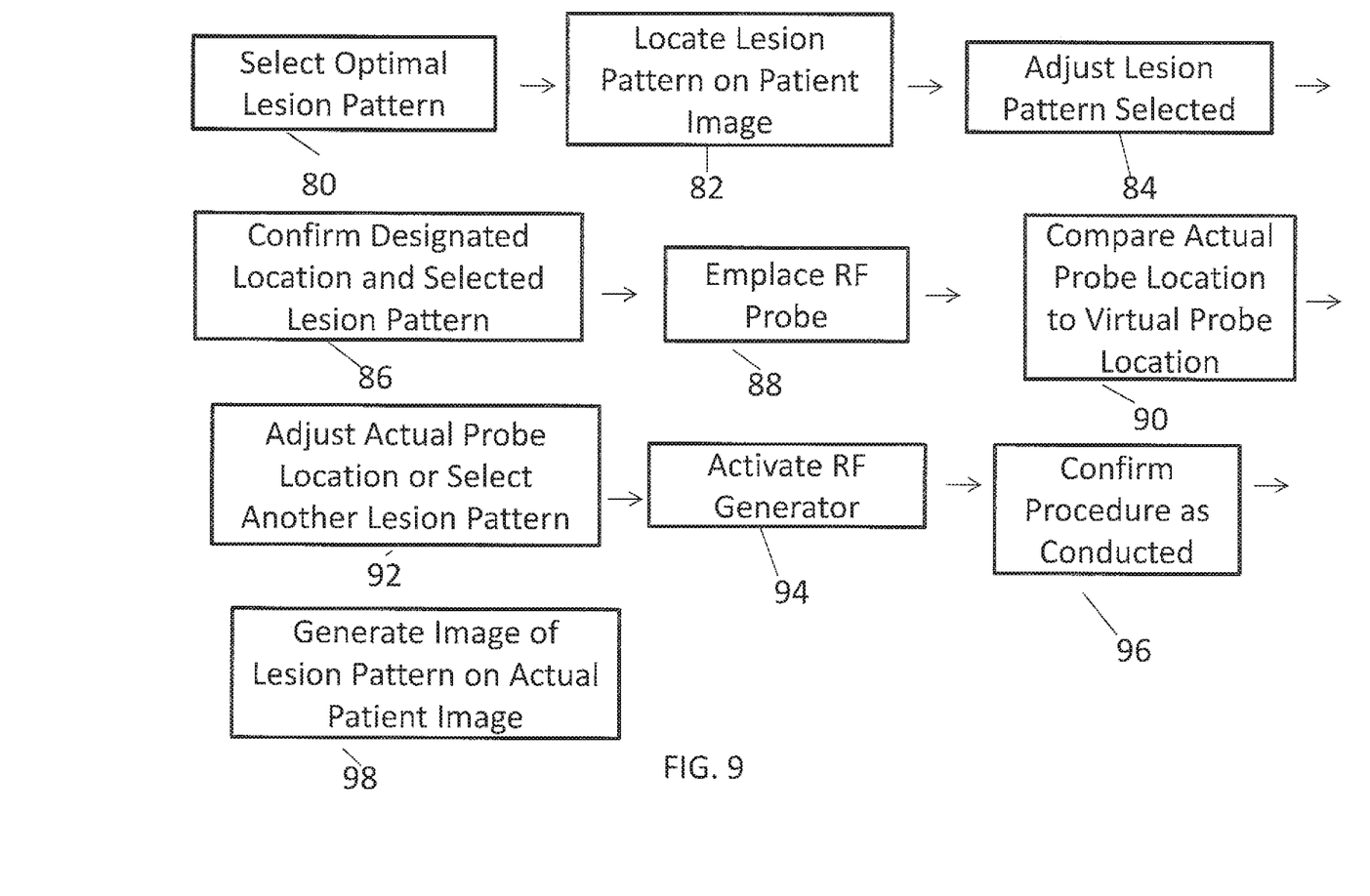
FIG. 9 is a flow diagram of a method of the invention.

Referring to FIG. 9, a method of the invention is provided in a flow diagram to describe steps associated in the method. This method may be considered a diagnostic method for the steps that do not involve actual patient treatment, and also a combined diagnostic method in which treatment is combined with the pre-procedure steps. At step 80, a practitioner selects an optimal lesion pattern. As mentioned, the lesion pattern comprises a virtual image provided on a user interface. The user interface can provide a menu option for many different lesion patterns with varying shapes and sizes. The user interface can provide dimensioning of the lesion patterns by length, diameter, circumference, or other geometric measurements. These measurements can be provided in units so that the practitioner can select exact dimensioning parameters. These units could include units in millimeters or other units of measurement. At step 82, the selected lesion pattern can be superimposed on a patient image. The patient image can either be a virtual image of the patient representative of the particular location on the anatomy of the patient which is to be treated. Alternatively, the patient image can be an actual image of the patient's anatomy taken prior to conducting the RFA procedure. At step 84, the precise location of the selected lesion pattern may be adjusted for optimal treatment. In this step, the particular location of the lesion pattern may be adjusted with respect to the patient image. If the practitioner is not satisfied with the selected lesion pattern, the practitioner has the option of selecting another lesion pattern. At step 86, a practitioner confirms the desired location and the selected lesion pattern. At this point, the corresponding RF generator settings are automatically confirmed so that delivery of energy is commensurate with the selected lesion pattern as well as the RF probe being used in the procedure. At step 88, the practitioner emplaces the RF probe. At step 90, the actual location of the emplaced RF probe may be compared to a virtual RF probe positioning location. A substantial alignment or overlap of the virtual RF probe and the actual emplaced RF probe may be used as a confirmation that the RF probe is correctly positioned. At step 92, the actual RF probe location may be adjusted as necessary to ensure the selected lesion pattern can be created. Alternatively, instead repositioning the RF probe, the practitioner may wish to select another lesion pattern based upon difficulty of repositioning the RF probe or other factors such as the particular anatomy of the patient. If another lesion pattern is selected, yet another virtual image of the selected lesion pattern is superimposed over the actual image of the patient with the RF probe as emplaced. At step 94, assuming the practitioner is satisfied with the selected lesion pattern and the location of the emplaced RF probe, the RF generator is activated to deliver RF energy according to the parameters selected for the particular procedure. At step 96, confirmation of the procedure is conducted by confirming the actual energy delivered by the RF generator according to the predetermined settings. At step 98, one or more images may be created which include actual images of the treated area of the patient and superimposed virtual images of the lesion pattern that was created according to the preselected lesion pattern.

It should also be understood that the images created in this method are not limited to a single lesion pattern, but may comprise more than one lesion created by the use of multiple RF probes. In the event of use of multiple RF probes, the practitioner may individually select the desired lesion patterns as corresponding to the particular RF probes to be used in the procedure. It should also be understood that the foregoing method is not strictly limited to each and every step as recited. For example, the adjustment steps of 84 and 92 may be considered optional in that recited adjustments may not be necessary. If multiple lesions are created, such as if the RF probe(s) are repositioned and repeat lesioning is performed, the system and method of the invention further includes generating virtual lesion images that take into account the combined individual lesions. In other words, the combined sizes and shapes of the lesions, and the extent to which they may overlap, can be presented in a user display and saved as a treatment record image showing the multiple lesions.

It should also be understood that the enhanced imaging provided by the present invention as applied to RFA procedures is distinct from electrostimulation procedures in which no ablation of tissue occurs. In electrostimulation, the goal is to electrically stimulate tissue with a permanently implanted device, primarily for healing purposes or to induce electrochemical neuromodulation, in which it is known that the electrical current supplied provides a therapeutic effect. The areas of tissue that can be treated by electrostimulation are significantly different than the areas of tissue that are treated by ablation under RFA procedures. Generally, electrostimulation is only capable of delivering optimal electrical current with areas confined directly in contact with the electrostimulation probe, and there is no consideration of particular tissue areas that need to be ablated to achieve denervation. In other words, destruction of nerves by denervation is not contemplated within electrostimulation which the opposite effect is desired, namely, to heal and/or stimulate nerve tissue.

Although the invention is described herein with respect to multiple preferred embodiments, the invention is not strictly limited to these embodiments and should rather be more broadly interpreted commensurate with the scope of the claims appended hereto.

What is claimed is:

1. A system for generating images representative of areas to be treated by radiofrequency (RF) ablation, comprising:
   a computer processor including a memory, a processing element, and programmable instructions including at least one mathematical relationship for visually modeling a size and shape of a selected lesion pattern to be created;
   an RF probe communicating with said computer processor;
   an RF generator for supplying RF energy to said RF probe;
   said mathematical relationship including variables incorporated in said mathematical relationship including (a) specifications for said RF probe to be used in an ablation procedure, (b) an amount of RF energy to be supplied through the RF probe during the ablation procedure, and (c) a measured amount of time in which the RF energy is to be supplied;
   a first visual display for viewing first virtual images corresponding to at least one selected lesion pattern to be created, said selected lesion pattern being depicted on said visual display as an object having a length, depth and width; and
   a second visual display including second virtual images of the lesion pattern size and shape as an ablation procedure takes place and wherein said second virtual images are progressive, time-based images in which a size of the lesion pattern is shown to increase over time as RF energy continues to be provided through said RF probe.

2. A system, as claimed in claim 1, wherein said visual display includes said object having a geometric shape corresponding to said at least one selected lesion pattern to be created.

3. A system, as claimed in claim 1, wherein said visual display further includes an image of anatomy of a patient undergoing the ablation procedure, and said at least one selected lesion pattern to be created is superimposed over the RF probe positioned in the patient such that the at least one selected lesion pattern to be created is a proposed virtual lesion pattern.

4. A subsystem for generating images representative of areas to be treated by radiofrequency (RF) ablation, comprising:
   a computer processor including a memory, a processing element, and programmable instructions including at least one mathematical relationship for visually modeling a size and shape of a selected lesion pattern to be created;
   said mathematical relationship including variables incorporated in said mathematical relationship including (a) specifications for an RF probe to be used in an ablation procedure, (b) an amount of RF energy to be supplied through the RF probe during the ablation procedure, and (c) a measured amount of time in which the RF energy is to be supplied;
   a first visual display for viewing first virtual images corresponding to at least one selected lesion pattern to be created; and
   a second visual display including second virtual images of the lesion pattern size and shape as an ablation procedure takes place and wherein said second virtual images are progressive, time-based images in which a size of the lesion pattern is shown to increase over time as RF energy continues to be provided through said RF probe.

5. A subsystem, as claimed in claim 4, wherein said visual display includes a geometric shape corresponding to said at least one selected lesion pattern to be created.

6. A subsystem, as claimed in claim 4, wherein said visual display further includes an image of anatomy of a patient undergoing the ablation procedure, and said at least one selected lesion pattern to be created is superimposed over the RF probe positioned in the patient such that the at least one selected lesion pattern is a proposed virtual lesion pattern.

7. A method for generating images representative of areas treated to be treated by radiofrequency (RF) ablation, comprising:
   providing a computer processor including a memory and a processing element; providing programmable instructions including at least one mathematical relationship for visually modeling a size and shape of a selected lesion pattern to be created;
   providing communications between an RF probe and said computer processor;
   generating power for delivery to said RF probe by an RF generator;
   determining in said at least one mathematical relationship a plurality of variables to achieve said modeling, said variables at least including (a) specifications for said RF probe to be used in an ablation procedure, (b) an amount of RF energy to be supplied through the RF probe during the ablation procedure, and (c) a measured amount of time in which the RF energy is to be supplied; and producing a first visual display including first virtual images corresponding to at least one selected lesion pattern to be created, said selected lesion pattern is depicted on said visual display as an object having a length, depth and width; and producing a second visual display including second virtual images of the lesion pattern size and shape as an ablation procedure takes place and wherein said second virtual images are progressive, time-based images in which a size of the lesion pattern is shown to increase over time as RF energy continues to be provided through said RF probe.

8. A method, as claimed in claim 7, wherein producing said visual display includes said object having a generating a geometric shape corresponding to said at least one selected lesion pattern to be created.

9. A method, as claimed in claim 7, wherein producing said visual display further includes generating an image of anatomy of a patient undergoing the ablation procedure, and said at least one selected lesion pattern to be created is superimposed over the RF probe positioned in the patient such that the at least one selected lesion pattern to be created is a proposed virtual lesion pattern.

10. A diagnostic method for generating images representative of areas to be treated in a subsequent radiofrequency (RF) ablation procedure, comprising:

providing a computer processor including a memory and a processing element;

providing programmable instructions including at least one mathematical relationship for visually modeling a size and shape of a selected lesion pattern to be created;

providing communications between an RF probe and said computer processor;

determining in said at least one mathematical relationship a plurality of variables to achieve said modeling, said variables at least including (a) specifications for said RF probe to be used in an ablation procedure, (b) an amount of RF energy to be supplied through the RF probe during the ablation procedure, and (c) a measured amount of time in which the RF energy is to be supplied; and providing a first user interface showing said at least one selected lesion pattern to be created in response to said modeling including showing said size and shape of said selected lesion pattern to be created;

selecting a desired lesion pattern to be created in the subsequent RF ablation procedure;

providing a second user interface with a composite image showing the selected lesion pattern to be created with an image of anatomy of a patient to be treated and the selected lesion pattern to be created positioned on the image of the anatomy at a desired location for subsequent treatment of targeted tissue, wherein said selected lesion pattern is depicted on said second user interface as an object having a length, depth and width; and producing a third user interface including images of the lesion pattern size and shape as an ablation procedure takes place and wherein said images of the lesion pattern are progressive, time-based images in which a size of the lesion pattern is shown to increase over time as RF energy continues to be provided through said RF probe.

11. A method for generating images representative of areas to be treated in a subsequent radiofrequency (RF) ablation procedure, comprising:

providing a computer processor including a memory and a processing element;

providing programmable instructions including at least one mathematical relationship for visually modeling a size and shape of a selected lesion pattern to be created;

providing communications between an RF probe and said computer processor;

determining in said at least one mathematical relationship a plurality of variables to achieve said modeling, said variables at least including (a) specifications for said RF probe to be used in an ablation procedure, (b) an amount of RF energy to be supplied through the RF probe during the ablation procedure, and (c) a measured amount of time in which the RF energy is to be supplied; and providing a first user interface showing said at least one selected lesion pattern to be created in response to said modeling including showing said size and shape of said selected lesion pattern to be created; and selecting a desired lesion pattern to be created in the subsequent RF ablation procedure;

providing a second user interface with a composite image showing the selected lesion pattern to be created with an image of anatomy of a patient to be treated and the selected lesion pattern to be created positioned on the image of the anatomy at a desired location for treatment of targeted tissue, wherein said selected lesion pattern is depicted on said second user interface as an object having a length, depth and width;

confirming the desired location and the selected lesion pattern to be created for determining RF generator settings to deliver RF energy commensurate with the selected lesion pattern to be created and the RF probe to be used in the procedure;

activating the RF generator to deliver RF energy according to parameters selected for the procedure; and providing a third user interface with a composite image including an actual image of the treated location of the patient and a superimposed virtual image of the selected lesion pattern created.

12. A method, as claimed in claim 11, further including:
confirming the actual RF energy delivered by the RF generator according to the predetermined settings.

13. A method for generating images representative of areas to be treated in a subsequent radiofrequency (RF) ablation procedure, comprising:

providing a computer processor including a memory and a processing element;

providing programmable instructions including at least one mathematical relationship for visually modeling a size and shape of a selected lesion pattern to be created;

providing communications between an RF probe and said computer processor;

determining in said at least one mathematical relationship a plurality of variables to achieve said modeling, said variables at least including (a) an amount of RF energy to be supplied through the RF probe during the ablation procedure, and (b) a measured amount of time in which the RF energy is to be supplied;

providing a first user interface showing said at least one selected lesion pattern to be created in response to said modeling including showing said size and shape of said selected lesion pattern to be created; and selecting a desired lesion pattern to be created in the subsequent RF ablation procedure;

providing a second user interface with a composite image showing the selected lesion pattern to be created on a selected area of an anatomy of a patient to be treated;

providing a depiction of the selected lesion pattern on said second user interface as an object having a length, depth and width;

confirming the desired location and the selected lesion pattern to be created for determining RF generator settings to deliver RF energy commensurate with the selected lesion pattern to be created and the RF probe to be used in the procedure;

activating the RF generator to deliver RF energy according to parameters selected for the procedure; and providing a plurality of additional user interfaces showing the composite image including an actual image of the treated location of the patient and a superimposed virtual image of the lesion pattern created as time progresses, the plurality of additional user interfaces differing by a size of the lesion pattern changing as time progresses.

* * * * *